United States Patent [19]

Morgan et al.

[11] 4,437,006
[45] Mar. 13, 1984

[54] METHOD AND APPARATUS FOR MEASURING RADIATION IN COMPUTER-ASSISTED TOMOGRAPHY AND RADIOGRAPHIC APPLICATIONS

[75] Inventors: Ira L. Morgan; E. C. George Sudarshan; Alvin L. Mitchell; James P. Coose; Hunter D. Ellinger; James W. Jagger, all of Austin, Tex.

[73] Assignee: Scientific Measurement Systems, Inc., Austin, Tex.

[21] Appl. No.: 260,695

[22] Filed: May 5, 1981

Related U.S. Application Data

[62] Division of Ser. No. 879,439, Feb. 21, 1978, Pat. No. 4,284,895.

[51] Int. Cl.³ .............................................. G01T 1/20
[52] U.S. Cl. ............................... 250/363 S; 250/367; 378/9
[58] Field of Search ............. 250/361 R, 360.1, 363 S, 250/366, 367, 368; 378/7, 9, 10, 147, 148, 165

[56] References Cited

U.S. PATENT DOCUMENTS

| | | | |
|---|---|---|---|
| 3,073,954 | 1/1963 | Carlson et al. | 250/368 |
| 3,778,614 | 12/1973 | Hounsfield | 378/7 |
| 3,866,047 | 2/1975 | Hounsfield . | |
| 3,924,129 | 12/1975 | Le May . | |
| 3,924,131 | 12/1975 | Hounsfield . | |
| 3,944,833 | 3/1976 | Hounsfield . | |
| 3,956,633 | 5/1976 | Hounsfield . | |
| 4,057,725 | 11/1977 | Wagner | 378/9 |
| 4,096,389 | 6/1978 | Ashe et al. | 378/147 |
| 4,185,195 | 1/1980 | Moore | 378/147 |
| 4,284,895 | 8/1981 | Morgan et al. | 378/9 |

Primary Examiner—Janice A. Howell
Attorney, Agent, or Firm—Jerry M. Keys

[57] ABSTRACT

An apparatus for determining the intensity of radiation passing through an object as a set of planar beams from a radiation source is disclosed. The radiographic apparatus includes a detector array of adjoining scintillators having wall linings suitable for absorbing radiation, thereby functioning as self-colliminating detectors. The apparatus is also capable of counting the number of individual photons of primary radiation passing through an object along each path from a radiation source operating at the very high count rates used in computer-assisted tomography applications.

16 Claims, 10 Drawing Figures

METHOD AND APPARATUS FOR MEASURING RADIATION IN COMPUTER-ASSISTED TOMOGRAPHY AND RADIOGRAPHIC APPLICATIONS

This is a division of application Ser. No. 879,439, filed Feb. 21, 1978, now U.S. Pat. No. 4,284,895.

BACKGROUND OF THE INVENTION

1. Field of the Invention

The present invention relates to a method of, and apparatus for, examining an object by means of penetrating radiation, such as X-rays or gamma-rays.

2. Description of the Prior Art

Considerable effort has been expended in recent years to develop a method and apparatus for accurately examining the detailed structure of the interior of a body by penetrating radiation which utilize principles of tomographic reconstruction. These efforts have been directed toward solving the problem of obscured details found in conventional X-ray or gamma-ray radiographic imaging. Such obscuring of details was caused by the superimposition of the other structural details of the body through which the radiation passed prior to detection.

The more recent developments are based upon the theoretical principles of computer-assisted tomography which have been recently summarized in a paper entitled "Principles of Computer Assisted Tomography (CAT) in Radiographic and Radioisotopic Imaging" by Rodney A. Brooks and Giovanni Di Chiro, published in Vol. 21, No. 5 at pp. 689-732 of PHYS. MED. BIOL. (1976) Specific methods and apparatus developed to employ these principles for medical applications are exemplified by U.S. Pat. Nos. 3,778,614; 3,866,047; 3,944,833; and 3,924,131. These patents disclose a method of exposing a planar slice of a body to penetrating radiation along a plurality of paths at different mean angular positions and detecting the radiation emerging from the body to estimate the radiation absorbed by the body along each path. The mean angular positions of each of the plurality of paths are so arranged so that such paths intersect every element of a two-dimensional array of elements (matrix) used to delineate the planar slice of the body.

The data representative of the radiation absorbed along each of the paths is then used to estimate the absorption coefficients of each element of the matrix by employing either iterative reconstruction techniques, as exemplified by U.S. Pat. No. 3,778,614; analytic reconstruction techniques (convolution function), as exemplified by U.S. Pat. No. 3,924,129, and combination analytic/iterative techniques, as exemplified by U.S. Pat. No. 3,924,129.

Various apparatus have also been developed to carry out the computer-assisted tomographic methods described above. In U.S. Pat. No. 3,924,131 a radiation source and a detector are mounted on a frame facing each other across an aperture in which the body is positioned so that the source and detector are moved together relative to the stationary body between different lateral positions so that the collimated radiation beam is scanned laterally to form a plurality of paths and then the frame rotated to other angular positions where additional lateral scanning is effected. In U.S. Pat. Nos. 3,866,047 and 3,944,833 a source transmitting a collimated fan beam of radiation toward the object and a bank of detectors positioned opposite the source are mounted on a turntable for orbiting the source and bank of detectors relative to the body. Other scanners have been developed which utilize a stationary circular array of detectors and the rotation of a single source along a circular path just within the circular array of detectors. All of these apparatus, however, involve movement of the source or detectors, or both, relative to the body being examined during a scan of a slice of the body. Such movement also limits the speeds at which the scanning can be accomplished. For example, movement makes it difficult to exactly determine the coordinate position of the ray paths, determine the exact position of the moving source or detector due to aberrations in the position of the source or detectors caused by the inherent variable movement of heavy mechanical devices when they are in motion, and high voltage connection problems caused by rotation of the source and/or detectors. Each of these problems reduce the accuracy of the data obtained for use in determining the absorption coefficients of the matrix elements.

Previous examining apparatus has also attempted to represent the radiation intensity detected by generating output signals representative of the total electrical charge generated by the detection system during an exposure, as exemplified by U.S. Pat. Nos. 3,778,614; 3,914,131; 3,866,047, and 3,956,633. Use of such current integration techniques to obtain output signals require high dosage levels in order for the intensity level emerging from the body to be detectable over the system's noise. The current integrating apparatus also induces measurement errors in the output signal. Moreover, the accuracy of the output signal is further degraded since the current integrated signal fails to account for statistical variations in the energy content of the photons detected. As a result such measurements cannot be used in applications to determine the exact number of photons detected.

Previous examining apparatus employing multiple detectors has also attempted to segregate the paths of radiation passing through the body to the detectors by using relatively bulky mechanical collimators, as exemplified by U.S. Pat. No. 3,866,047. Such collimators prohibit the placement of detectors in high-density detector arrays, thereby requiring a longer exposure time or an increase in the number of scans in order to obtain sufficient information for an adequate reconstruction.

Other apparatus and methods employed in the examination of a body using reconstructive tomography are illustrated in U.S. Pat. Nos. 3,778,614; 3,866,047; 3,944,833; 3,867,634; 3,919,552; 3,924,131; 3,881,110; 3,965,357; 3,936,636; 3,924,129; 3,932,757; 3,952,201; 3,973,128; 3,946,234; and 3,956,633.

Finally, recent scientific experiments have been conducted to evaluate the feasibility of using plastic scintillators for low energy, high rate photon detection, as shown by an article entitled "Comparative Studies on Plastic Scintillators—Applications to Low Energy High Rate Photon Detection" by L. A. Eriksson, C. M. Tsai, Z. H. Cho, and C. R. Hurlbut, published at pp. 373-376 in Vol. 122 of NUCLEAR INSTRUMENTS AND METHODS (1974). The experiments discussed in the above-referenced article, however, were conducted with only monoenergatic radiation. Furthermore, so far as is known, there has been no previous use of such high-speed plastic scintillators in apparatus for tomographic examination of an object by means of penetrating radiation.

SUMMARY OF THE INVENTION

Briefly, the present invention provides a new and improved method of, and apparatus for, examining at least part of an object using penetrating radiation, such as X-rays or gamma rays, which provides more accurate information for a given radiation intensity and decreases the time necessary to conduct the examination. The novel method comprises transmitting photons of penetrating radiation toward a planar section of the object under examination wherein a portion of the photons transmitted pass through the planar section of the object as photons along a plurality of paths, detecting the plurality of photons passing through the object along each of the plurality of paths, counting the number of photons detected, and generating output signals representative of the number of photons detected.

The novel apparatus includes a radiation source for transmitting photons of penetrating radiation through a planar section of the object along a plurality of paths and a detector system disposed on the opposite side of the object from the source for detecting the plurality of individual photons emerging from the object along the plurality of paths. The detector system also generates a plurality of detector signals representative of the radiation detected.

Preferably, the new and improved apparatus includes a plurality of radiation sources angularly disposed at intervals about the object to be examined for transmitting photons of penetrating radiation through the planar section of the object and a plurality of detector systems disposed at intervals about the planar section of the object for detecting the plurality of photons transmitted by the sources. Each of the detector systems is disposed directly opposite one of the sources for individually detecting the plurality of photons in each of the set of rays being transmitted from the source opposite it.

Also, each detecting system is preferably self-collimating so that it detects only photons whose paths are within a small angular deviation from a path which is perpendicular to its detecting surface. The self-collimating detecting system is disposed so that the paths of the plurality of penetrating rays photons passing through the object from the source opposite it are substantially perpendicular to said detecting surface.

The invention also provides a novel method of detecting the intensity of penetrating radiation passing through an object along a plurality of paths from a radiation source which comprises detecting individual penetrating ray photons passing through the object along one of the plurality of paths, converting each individual penetrating ray photon detected into a plurality of light photons within a suitable time interval after detection such that substantially all light photons associated with each of the penetrating ray photons detected are generated within different time intervals, detecting the plurality of light photons generated by the conversion of each of the penetrating ray photons, generating a primary signal for each plurality of light photons detected, counting the number of primary signals generated, and generating an output signal representative of the number of primary signals generated. The resulting output signal is representative of the intensity of the penetrating radiation which passed through the object along one of the plurality of paths.

It also provides for novel apparatus for detecting the intensity of the penetrating radiation passing through an object along a plurality of paths from a radiation source.

Such apparatus includes a scintillator which detects the plurality of ray photons passing through the object along one of the plurality of paths. This scintillator also converts each of the ray photons detected into a distributed bundle of light photons within a suitable time interval after detection such that a substantial portion of the light photons associated with each detected penetrating ray photon are generated within different time intervals. A photomultiplier optically coupled to the scintillator detects the bundle of light photons associated with each penetrating ray photon detected and thereafter generates a signal for each bundle of light photons associated with the detection of a penetrating ray photon. A counter counts the signals generated by the photomultiplier and generates an output signal representative of the number of penetrating ray photons detected by the scintillator.

It is an object of this invention to provide a simpler and faster method of, and apparatus for, measuring small differences in the absorption coefficient, and spatial locations of such differences, in a planar slice of a body without an increase in the amount of radiation used to scan the object.

Another object is to provide a method of, and an apparatus for, counting the individual photons of radiation emerging from a body along a path.

BRIEF DESCRIPTION OF THE DRAWINGS

FIG. 7b is a side section view of the scanning apparatus of FIG. 7a;

FIG. 8a is a side elevation view of a portion of one type of detecting apparatus to be mounted on the scanning apparatus shown in FIG. 7a; and FIG. 8b is a front elevation view of the portion of one type of detecting apparatus shown in FIG. 8a.

DESCRIPTION OF THE PREFERRED EMBODIMENT

Figure 1:
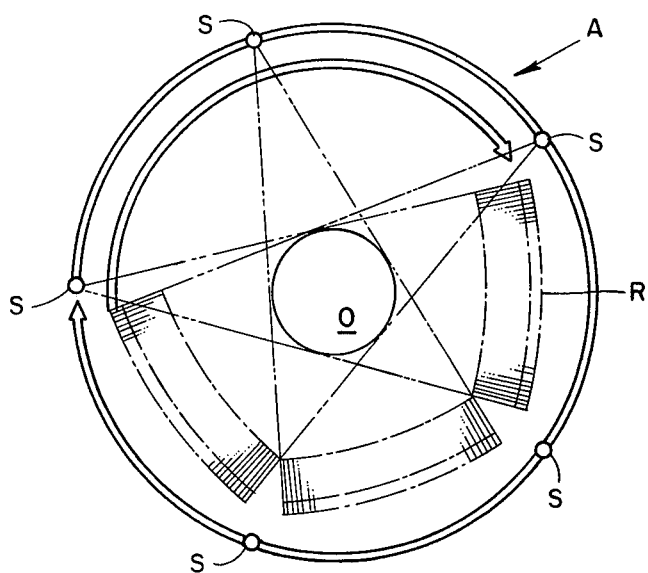
FIG. 1 is a simplified diagrammatic representation of a suitable scanning apparatus for carrying out the present invention.
Figure 2:
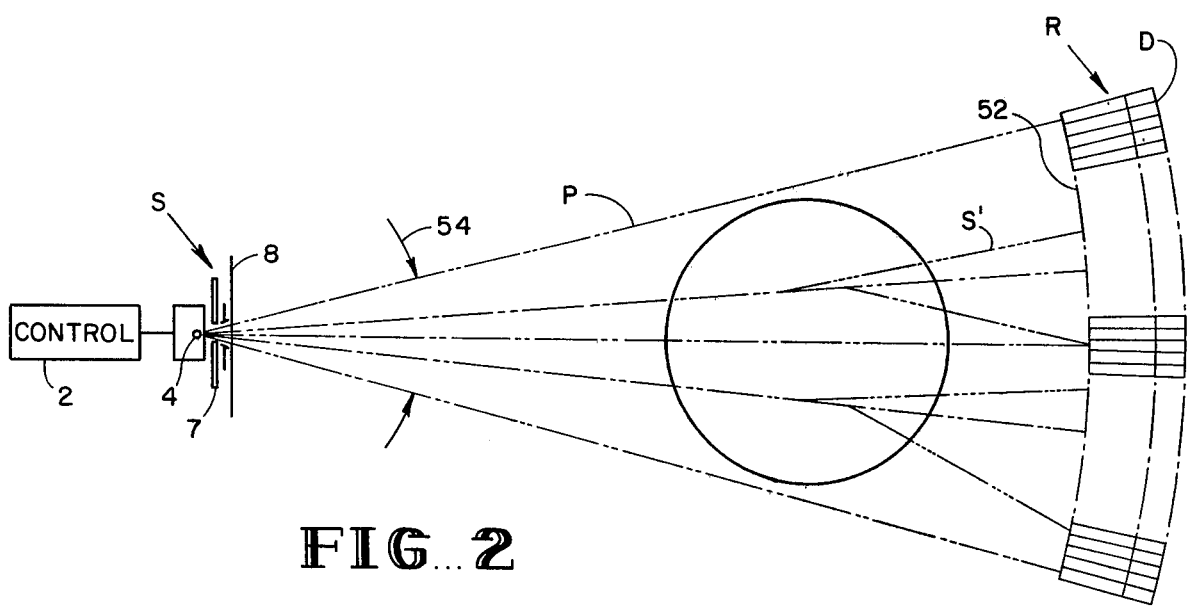
FIG. 2 is a simplified diagrammatic representation of a portion of the scanning apparatus of FIG. 1.
Figure 4:
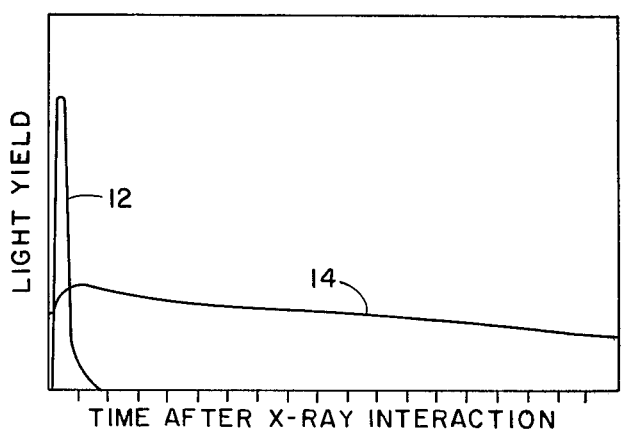
FIG. 4 is a graphical comparison of materials useful in constructing the scintillator shown in FIG. 3.

In the drawings (FIGS. 1, 2, and 4), a scanning apparatus A has a plurality of radiation sources S mounted on suitable mounting apparatus A at intervals about the object O to be examined. Preferably, 2N+1 sources are disposed about the object, where N is any integer. FIG. 1 illustrates one embodiment of such examining apparatus which utilizes 5 sources. Each of the sources S are disposed in the same plane in order that each source S can transmit a planar swath of penetrating radiation, such as X-rays or gamma rays, through a planar section of the object O to obtain a scan of the object. The penetrating radiation forming the swath of radiation may be described as a plurality of photons traveling along each path of a plurality of paths.

A portion of the penetrating radiation transmitted, hereinafter described as secondary photons, are either absorbed by the object or deflected from the original paths to travel in any direction from the point of deflection along secondary paths S. The remaining portion of the photons, hereinafter described as primary photons, originally transmitted by the source along a given path pass through the object without being deflected or absorbed by the object and continue along their original line of travel or path P to one of a plurality of detectors D arranged in an array R of detectors. The photons deflected to become secondary photons have less energy after deflection than that of the primary photons. The array R of detectors D is disposed to detect primary photons emerging from the object from the source S directly opposite the array R.

Each detector D of the array R is self-collimating such that it detects only photons of penetrating radiation which have paths which are substantially perpendicular to the surface of the detector D facing toward the source S opposite it. Hence, substantially all of the photons detected by each of the detectors D in any array R are primary photons which have traveled from the source S opposite it through the object O along its original ray path P.

Each detector D detects individual photons of radiation during the time interval the source opposite it is on and generates an output signal which is representative of the total number of photons detected. This output signal, in turn, may be used to obtain a signal representative of the radiation absorption which has occured along the original path P between the source S and the detector D opposite it when the initial intensity of the penetrating radiation from the source S is known.

Figure 7B:
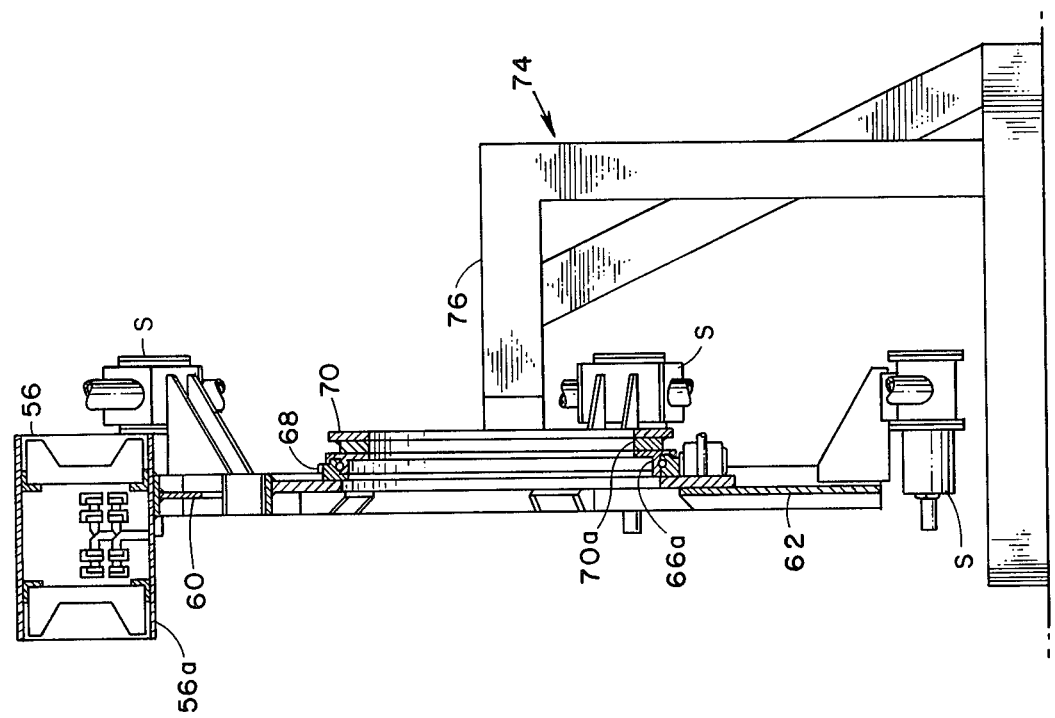
Figure 7A:
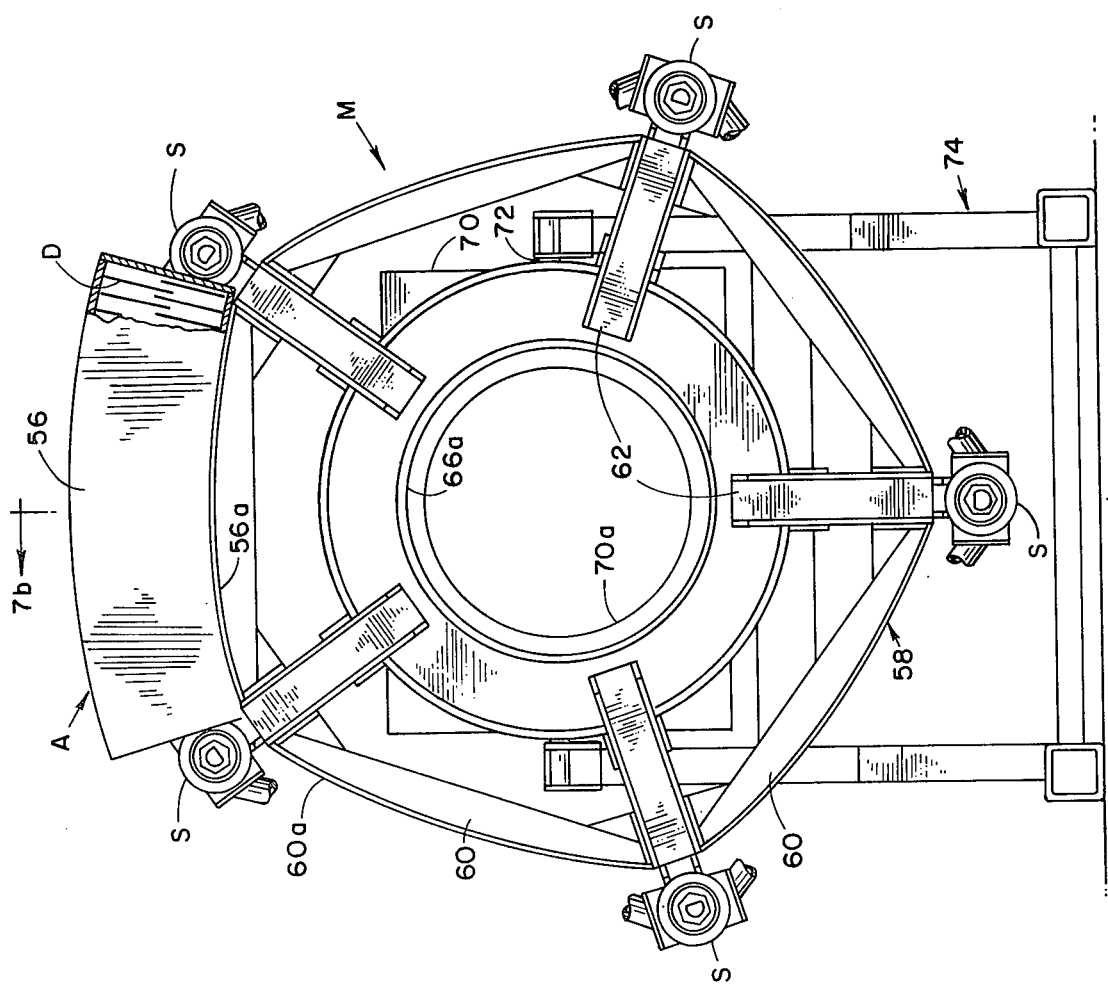
FIG. 7a is a front elevation view of a suitable embodiment of the scanning apparatus shown diagrammatically in FIG. 1.

Each of the detectors D in each array R is positioned so that the detecting surface of the detector is substantially perpendicular to one of the original ray paths P from the source S through the object O to the array R. The arrays R are also mounted on a suitable mounting apparatus M (FIG. 7a & 7b) in order to prevent any relative movement between the sources and detectors and between the object and either the sources or detectors during a scan of the object.

Figure 3:
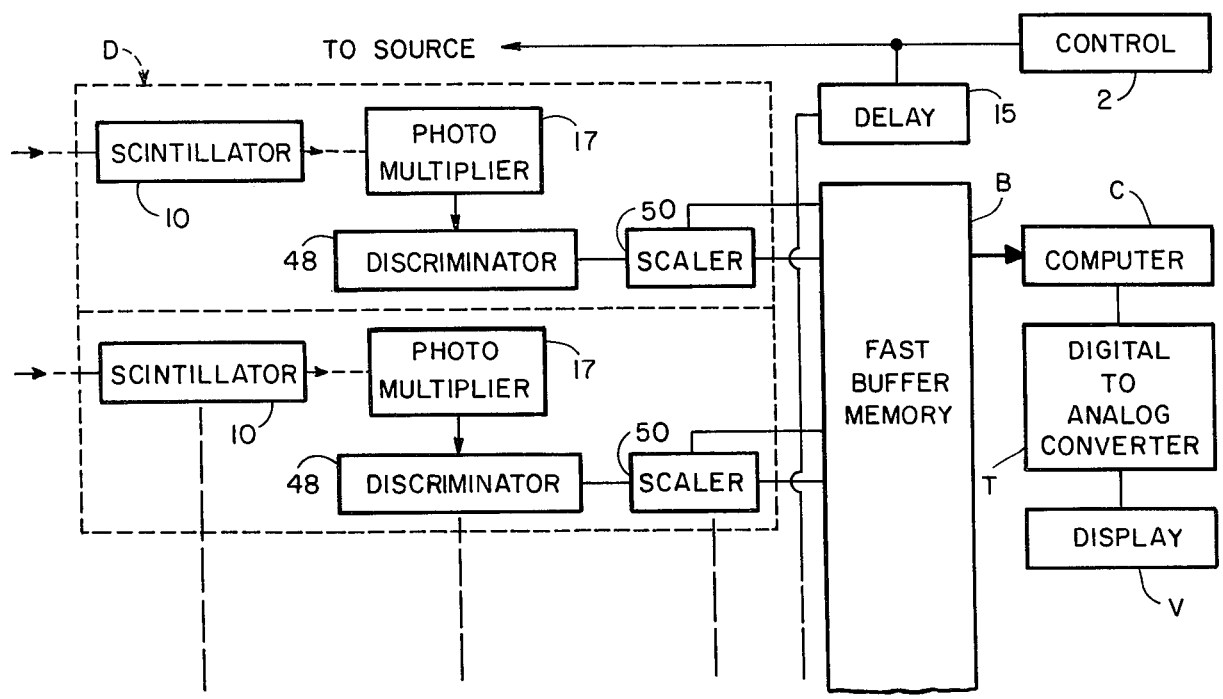
FIG. 3 is a schematic diagram of the part of the apparatus of the present invention for detecting penetrating radiation and processing the output signals representative of the radiation detected.

During a scan, a control circuit 2 (FIG. 2) controls the sequence and time duration of the transmissions from each of the sources S. Preferably, the control circuit sequentially pulses the sources on in a predetermined manner for a given time period, 100 milliseconds, for example. During the time a given source is on, the detectors D (FIG. 3) in the array A opposite it are also activated by the control circuit. The detectors D generate output signals in response to the radiation detected by each and these signals are fed to a temporary storage unit or fast memory buffer B for temporary storage. After the termination of transmission from a given source S, the output signals in the buffer B are fed to a computer or microprocessor C for initial error corrections and storage.

If desired for the particular type of examination, after transmitting radiation from each of the sources S, the scanning apparatus A may be rotated so that each of the sources can transmit radiation through the same planar section from other angular positions and thereby obtain additional information.

Subsequently, the mounting apparatus M can be inclined so that exposures of other planar sections can be obtained and output signals representative of such planar sections fed to the computer C. The output signals processed and stored within the computer for each planar section can then be evaluated to obtain digital signals representative of the coefficient of radiation absorption of different elements of the object. These digital signals can then be converted by a digital-to-analog converter T to analog signals useable by a display apparatus for visually displaying the relative absorptions of various portions of the object.

It has been found that the signals generated using the apparatus A of the present invention provide more useable information content and more accurate information per incident photon than prior examining apparatus regarding the radiation absorption characteristics of volume elements of an object. Furthermore, accurate information content for areas as small as one millimeter may be obtained.

The present invention is adaptable for use in such medical applications as distinguishing between tumors and normal tissue. It is also adaptable for use in many industrial applications, such as distinguishing between different layers of distinct materials within an enclosed structure.

I. SOURCE

Considering the apparatus of this invention in more detail, the source S (FIG. 2) may be a point source 4 situated in a source housing 6 having a suitable aperture through which the radiation is emitted. A fan collimator of conventional design may be disposed in front of the aperture to collimate the radiation to form a fan beam. Preferably, a baffled slot collimator 7 is used to form a fan beam with negligible penumbra. The construction of a baffled slot collimator is known to persons skilled in the art of nuclear physics. A suitable filter 8 may be used in connection with point sources emitting photons of varying energy content to filter out low-energy radiation which may cause surface burns to human or animal tissue.

The point source 4 may be an isotopic radioactive source, such as $AM^{241}$ or $IN^{192}$, which emits gamma rays, or a X-ray tube which emits variable energy X-rays. In the examination of inanimate objects, such as in industrial applications, isotopic radioactive sources are very useful, although their maximum intensity per unit is much less than X-rays tubes, since the exposure time can be relatively long in comparison with the short exposure times required for medical applications. Furthermore, such sources require no external power and emit photons of constant energy. The use of such monoenergetic photons are advantageous in that the problem of "beam hardening" associated with the broad energy spectrum of X-rays photons emitted by a X-ray tube is eliminated.

For medical applications, the source S is preferably a low intensity high-voltage X-ray tube. Low intensity X-ray tubes are preferable to isotopic radioactive sources for medical applications since the intensity of the isotopic source is insufficient in most cases to provide the short-term radiation dosage required for medical applications. Also, using several low intensity X-ray tubes are preferable to using one high intensity X-ray tube since such tubes have a longer useful life and require less maintenance. A suitable X-ray tube is a 40–150 KV variable intensity vacuum discharge X-ray tube manufactured by Amperex Corporation which has been modified so that it can be pulsed on for a short time interval, such as between 1 microsecond and 100 milliseconds. It should be understood, however, that other X-ray tubes and pulse intervals may be used.

II. DETECTOR

Each of the detectors D comprising the detector array R detects penetrating ray photons whose paths are substantially perpendicular to the surface of the detector. Each detector is the array R, in turn, is mounted in the detector array such that the detecting surface is substantially perpendicular to the line of travel P between the detector and the source S located directly opposite the detector such that substantially all the photons detected are primary photons which have traveled from the source opposite the detector D.

Each detector D includes a high-speed scintillator 10 (FIG. 3) with very fast decay times which converts a detected photon into a plurality of light photons within an interaction time interval or decay time of sufficiently short time duration such that the scintillator converts a substantial portion of the energy of the penetrating ray photon detected into light photons before the generation of light photons by a subsequently detected penetrating ray photon. It has been found that a material commonly described as scintillating plastic, manufactured by Nuclear Enterprises of San Carlos, Calif. as NE102A, NE106, NE111, and NE140 has such a sufficiently short decay time. The decay time distribution function of scintillating plastic designated as NE102A is shown as curve 12 in FIG. 4. Alternately, the scintillator may be made from stilbene, silicon, or other suitable materials having the requisite short decay time.

The advantages resulting from the use of such a material is easily shown by comparing the decay distribution function 12 of the scintillating plastic to the decay distribution function 14 of sodium iodide (NaI) crystals. Although sodium iodide crystals have been used in the past as scintillators for detecting penetrating radiation, such crystals have proved to be too slow to permit individual photon counting of X-rays photons at the fast counting rates required for certain applications, such as medical applications. Further NaI crystals have been used in conjunction with current integration apparatus which measures the total charge during each exposure shot. This total charge was used to determine the total energy of the X-rays received during an exposure, which in turn, was used to estimate a certain number of X-rays. The advantages of photon counting over current integration will be discussed in detail hereinafter. The advantages of using such short decay time scintillators are especially pronounced in the development of X-ray examining apparatus for use in medical applications where reductions in dosage are considered extremely beneficial.

It should also be noted that each scintillator 10 detects both primary photons and secondary photons as long as the photons are within a small angular deviation from the line of travel perpendicular to the detecting surface of the scintillator. Since the secondary photons have less energy than the primary photons, the number of light photons generated by each of the secondary photons is less than the number generated by each of the primary photons.

Due to the rapid decay time of such fast scintillating material, the ray photons detected by the scintillator within a given exposure will each generate a bundle of light photons. These bundles of light are then optically coupled to a photomultiplier 18 such that the bundles of light strike the photomultiplier in rapid succession. The photomultiplier 17, in turn, generates an electrical signal having an intensity proportional to the intensity of the light photons detected. Hence, the photomultiplier generates a signal of varying magnitude which has peaks associated with the bundles of light photons.

The signal from the photomultiplier 17 is fed to a discriminator 48 which electronically measures the magnitude of the electrical inpulses from the photomultiplier and generates output pulses when the intensity of the input pulses are above a threshold level. The discriminator is calibrated prior to actual use to determine the appropriate threshold level for the particular source energy spectrum so that the discriminator 48 detects only signal magnitudes above magnitudes associated with secondary photons and/or noise. Preferably, the discriminator includes a pre-stage amplifier to facilitate pulse recognition. Thus, the discriminator 48 generates output pulses for each of the primary photons detected and transmits these pulses to a scaler 50 which counts the output pulses to determine the number of primary photons which interacted with the scintillator 10 during a given exposure shot. The scaler, however, only counts pulses after receiving a signal from the control circuit 2, which is delayed by delay circuit 15 for a time determined by the time period between source pulses. The scaler, in turn, transmits a digital signal representative of the number of primary photons detected to the memory buffer B where the signal is temporarily stored for later transmission to the computer C. It will be appreciated that similar digital signals are transmitted to the fast memory buffer B from other detectors D forming the detector array R situated opposite the transmitting source.

There are numerous advantages of using photon counting methods and apparatus rather than current integration methods in examining an object with penetrating radiation whether the object is a animal or an inert industrial product. First, the photon-counting apparatus is theoretically capable of determining the exact number of primary photons detected. Moreover output signals generated by photon counting give more useable signal above the noise of the system for a given intensity; i.e., more information content. Noise other than sampling error is generated by a variety of phenomena, e.g., detector noise, thermal noise, noise due to motion, and noise from electronic equipment. Such noise generates extra current in current integration systems due to the long sampling time of approximately $10^{-2}$ seconds. Most of this current-producing noise is eliminated in photon counting due to the short sampling time such systems are capable of employing, $10^{-8}$ seconds, for example. It should be noted that the current integration apparatus itself also generates noise which affects the output signal.

Lastly, many applications require the use of X-ray tubes which produces a distributed energy spectrum of photons. Current integration systems attempt to measure the total energy of the X-rays received during an exposure or sampling interval. This total energy is then used to estimate a certain number of X-rays detected. Due to the variations in the accuracy of this estimate, the accuracy of the current integration system is degraded.

It should be understood that the method and apparatus for photon counting heretofore described may be used in various methods and apparatus for examining an object. For example it may be used with the examining apparatus disclosed in U.S. Pat. Nos. 3,778,614; 3,944,833; and 3,924,131.

Preferably, the scintillators 10 of each Detector D are self-collimating scintillators which detect only penetrating ray photons whose paths are within a small angular deviation from a line of travel which is perpendicular to the scintillator's detecting surface. It has been found that scintillating plastic which has been cut to a particular geometric configuration and has had several of its exterior surfaces coated with suitable material to optically decouple each scintillator from other scintillators located adjacent thereto in the detector array R are self-collimating.

Figure 5:
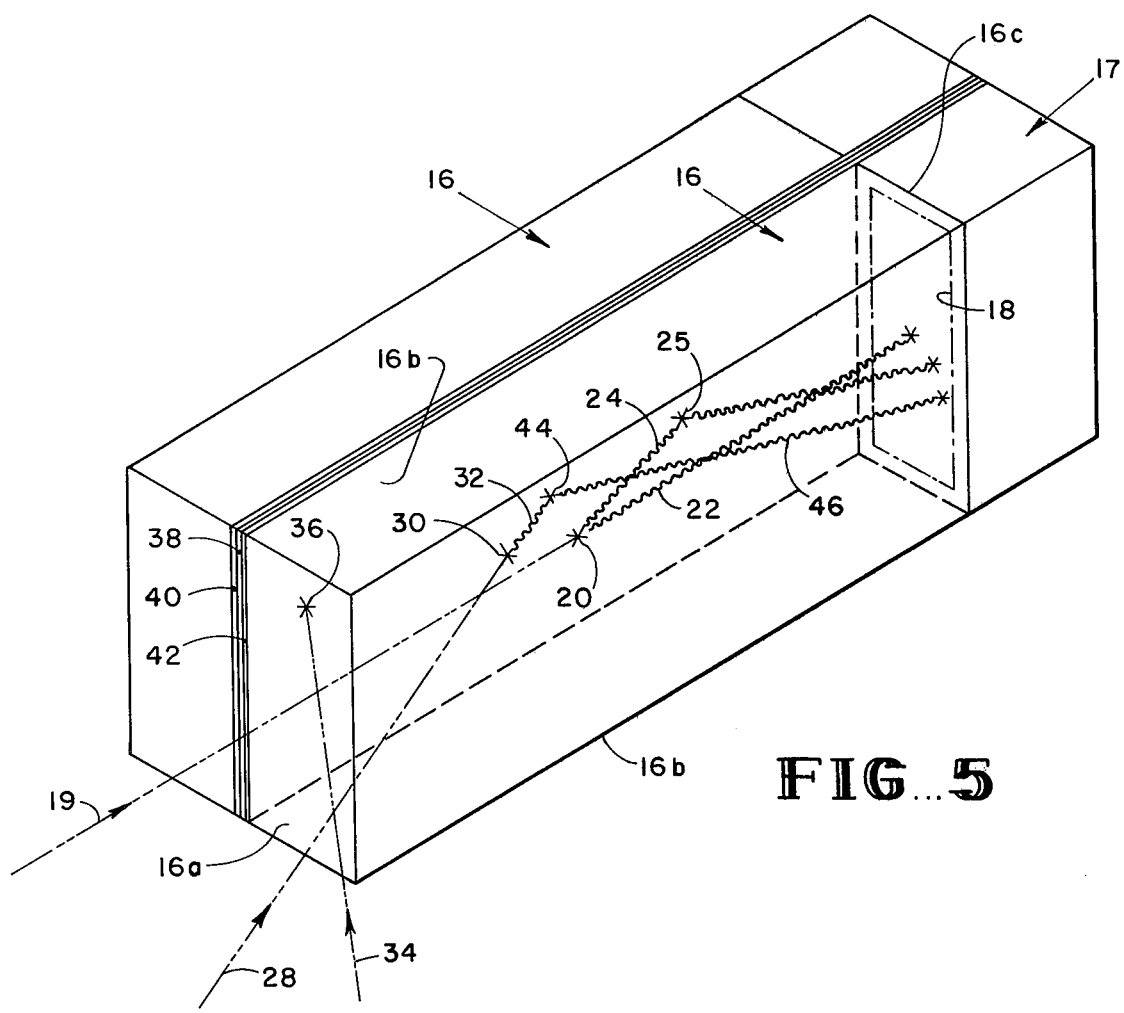
FIG. 5 is a diagrammatic representation of the interaction of penetrating rays with the scintillator shown in FIG. 3.

A suitable self-collimating scintillator (FIG. 5) includes a block 16 of scintillating plastic material having a detecting surface 16a of suitable height and a width which is dependent upon the distance of travel between the detector and the source S opposite the detector. For a distance of travel of approximately 180 centimeters, a suitable width is 4 millimeters. The depth of the scintillating block must be of sufficient length to allow penetrating ray photons whose paths are within a small angular deviation from a line perpendicular to the detecting surface to travel a sufficient distance within the block 16 to interact, scintillate, and convert a substantial amount of the energy of the ray photon to light photons.

The block 16 has lateral surfaces 16b which face adjacent blocks 16 and a back surface 16c optically coupled to a conventional photomultiplier 17. The photomultiplier has a photocathode 18 which initiates an avalanche of electrons when it is hit by a light photon passing through the back surface 16c from the scintillator 10.

The process of detection of penetrating ray photons by the scintillating plastic and the subsequent conversion of the energy into light photons is hereinafter illustrated by way of example. A penetrating ray photon having a path 19 which is perpendicular to the detecting surface 16a enters the scintillating plastic through the detecting surface and travels to a point 20 before the X-ray sufficiently excites the scintillating plastic to generate a distributed bundle of light photons. The various light photons generated then travel along various paths, such as paths 22 and 24 until they reach points on the back surface 16c and lateral surface 16b, respectively. The light photon along path 22 passes through the back surface and strikes the photocathode 18 of photomultiplier 17. The light photon along path 24 is reflected from the wall at a point 25 along path 26 along which the photon travels until it hits the photocathode 18.

Another photon traveling along a path 28 at a small angular deviation from a line perpendicular to the detecting surface 16a will travel to a point 30 before its energy begins to be converted into light photons. The various light photons generated will then travel along various paths, such as path 32. A photon traveling along a path 34 having a greater angular deviation from the line perpendicular to the detecting surface 16a, however, will not travel a sufficient distance by the time it reaches the lateral wall 16b at the point 36 to scintillate; consequently, penetrating ray photons at such an angle will not be detected by the scintillating block 16.

An absorption lining 38 is disposed between the lateral surfaces 16b of adjacent blocks 16 of scintillating plastic. A suitable lining is a piece of lead foil having a thickness of less than 1 millimeter. The lining 38 prevent penetrating ray photons, such as photons traveling along path 34 which do not interact with the scintillating block 16, from entering adjacent blocks 16 and generating light photons therein. In summary, the lining 34 decouples adjacent scintillators so that substantially all the secondary radiation entering the scintillator 10 is not detected by the detectors D and, therefore, does not induce errors as to the output signals from the detectors D as to the number of photons passing through the object along a given path.

Preferably, narrow layers 40 and 42 of reflecting material, such as aluminum, are positioned between the absorption lining 38 and the lateral surfaces 16c of the adjacent scintillating blocks 16 so that each scintillating block also collimates the light photons generated by the penetrating ray photons. For example, a portion of the light photons generated by the ray photon traveling along path 28 continue along path 32 from the point 30 to a point 44. At this point, a substantial portion of the light photons are reflected due to the differences in refraction coefficients of the scintillating block 16 and other materials next to it. The remaining portion of the light photons, however, would continue along path 32 without the presence of the reflecting material 42, which reflects a high percentage of the remaining portion of the light photons. Hence, essentially all light photons generated by the photon which are traveling along path 22 are reflected at the point 44 to travel along a path 46 until the light photons strike the cathode 18 of the photomultiplier 17 optically coupled to the scintillator. The use of a scintillator which self-collimates the generated light photons also permits the use of a photomultiplier having a recessed cathode. Such photomultipliers are less expensive and, consequently, the cost of a detector D can be reduced accordingly.

It should be noted that materials other than scintillating plastic may be used to construct a self-collimating scintillator. The geometric dimension of block of such other material may, of course, vary from those described above for scintillating plastic.

III. DETECTOR ARRAY

Detectors D which are self-collimating as discussed hereinabove may be arranged in the detector array R so that the entire array R is self-collimating. To construct the self-collimating array, each of the detectors D in each array R is positioned so that the detecting surface of each detector D is substantially perpendicular to one of the original ray paths P traveled by primary rays from the source S through the object O to the array R. Hence, the shape of the detector array R is dependent upon the orientation of the sources S relative to each other and to the object O and the pattern made by the paths P of primary photons passing through the object O. For example, if the ray paths from a source S are parallel, the scintillators 10 of the detectors D would be grouped such that the detecting surfaces 16a of the scintillators 10 would form a flat plane perpendicular to the parallel ray paths from the source S.

Preferably, 2n+1 sources S (FIG. 2) are mounted at fixed intervals about the object on a mounting apparatus M to be described in more detail hereinafter. Each of the sources S, in turn, emit planar swaths of radiation which are fan shaped so that a fewer number of sources S are required to obtain accurate information from a scan of the object O. For such a source, a suitable number of detectors D would be positioned into an array such that the detecting surfaces 16a of the scintillators 10 would form a curvilinear surface having a curvature determined by the locus of an arc 52. The arc 52, in turn, has as its center the point source 4 and has an arc length determined by the angle 54 defining the outermost paths in the fan-shaped set of primary ray paths P and the distance from the point source 4 to the detector array R.

In one suitable embodiment (FIG. 7a and 7b), the detectors D in the array R are mounted in a container 56 having a side 56a facing the source S opposite it which is transparent to penetrating rays. The container 56 is mounted to the mounting apparatus M in a manner to be described in more detail hereinafter such that the detecting surfaces 16a of the scintillators 10 in the array R form the curvilinear surface along arc 52 described hereinabove. It should be understood that other containers 56 containing detector arrays R are also mounted on the mounting apparatus M opposite each of the sources S mounted thereon.

Figure 8A:
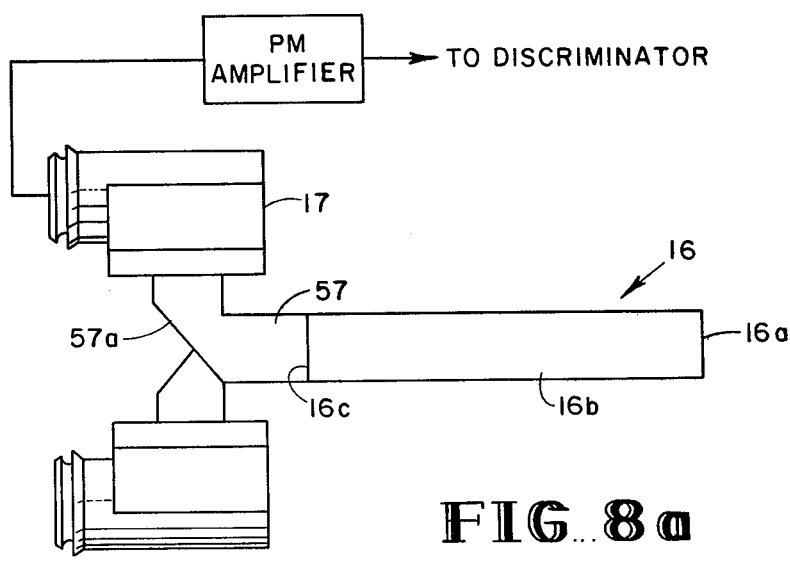
Figure 8B:
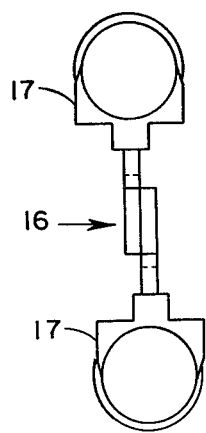

Preferably, the detectors D mounted in each of the arrays R have the scintillators 10 so configured such that the photomultiplier tubes 17 associated with adjacent scintillators 10 can be positioned in different planes. This permits the packing density of the detectors 10 in the array R to be increased since the photomultiplier tubes have a greater width than that commonly used for the scintillators 10. In one suitable configuration (FIG. 8a and 8b) one extension of an L-shaped piece of lucite or other material suitable for use as a light conduit can be attached by conventional means to the back surface 16c of the scintillating plastic 16 so that the light photons generated by the interaction of the penetrating ray photons with the scintillating plastic pass through the back surface 16c of the scintillating plastic 16 into the material 57 instead of directly to the photocathode of a photomultiplier tube 17. Such material 57 has the right angle portion of the L-shaped material cut away to form a reflecting surface 57a which reflects the light photons from the plane in which the scintillating plastic 16 is located either upward or downward along the other extension of the material 57 into the photocathode of the photomultiplier tube 17.

Alternately, scintillating plastic 16 from which the scintillator 10 may be formed can be cut to the configuration shown for the light collimating material 57. Such a unitary piece of scintillating plastic 16 both collimates the light photons generated in the scintillating plastic and reflects the collimated light photons either upward or downward into a photomultiplier tube 17 located in a different plane from that in which the scintillators 10 are located.

It has been found that self-collimating scintillators can be packed immediately adjacent each other using the packing configuration described hereinabove. By placing a detector having a straight block of material 57 optically coupling a block 16 to a photomultiplier 17 in the same plane between two detectors have extensions of L-shaped material 57 pointing upward and downward from the detector plane, a 3 detector configuration of high packing density is obtained. This 3 detector configuration may be repeated to form a complete array R. Thus, such a configuration of the scintillators 10 and photomultiplier tube 17 permits a denser packing of detectors which, in turn, permits the detection of a higher percentage of the primary photons having paths which are intercepted by the detector array R. Hence, more information about the radiation absorption by the object can be obtained for the same initial radiation intensity.

IV. MOUNTING APPARATUS

In one suitable embodiment (FIG. 7a and 7b) of the examining apparatus of the present invention, five sources S and five corresponding detector arrays R located in containers 56 are rigidly mounted to a mounting apparatus M by conventional means so that the sources S and arrays R do not move relative to each other. The mounting apparatus M includes an outer pentagonal-shaped supporting ring 58 onto which the sources S and corresponding detectors arrays R are mounted. Support members 60 are connected at each end to other support members 60 to form the pentagonal-shaped supporting ring 58. The sources S are mounted at each of the junctions of the support members 60 and a corresponding detector array R is mounted along the support member 60 opposite the junction on which a source S is mounted such that the planar swath of radiation from such source is detected by detectors D in such array R. Each support member 60 has an outer surface 60a to which the container 56 containing the detector array R is attached for mounting the container 56. It should be noted that the outer surface 60a is formed in the shape of an arc which fits into the arc 52 formed by the container so that each detector D in the array R is perpendicular to the paths P of primary photons coming from the source S opposite the detector.

One end of a supporting arm or strut 62 is connected to the supporting ring 58 at each of the junctions between adjacent support members 60 such that the other end of the strut 62 extends directly inward toward the center of the pentagonal-shaped ring 58. The inner portion of each of the struts 62 is connected to an inner circular ring 66 by suitable means. This circular ring has an inner edge 66a which defines a opening through which an object can be inserted for conducting an examination of the object. Preferably, the circular ring 66, in turn, is mounted on a ring gear assembly 68 situated between the circular ring 66 and a support plate 70 so that the circular ring 66, pentagonal-shaped supporting ring 58, and the sources S and detector arrays R mounted on the supporting ring 58 can be rotated relative to the support plate 70 when the ring gear assembly 68 is operated by a suitable driving means. Such a rotational capability allows additional scans of the object with the five sources at different mean angular positions, thereby effectively increasing the information content obtainable using five sources to that obtainable using a much greater number of sources S. For example, if the sources are rotated at 3 degree increments, the information content obtainable would be equivalent to have a scan using 120 different sources. It should be understood, however, that a different number of sources S other than five may be mounted at intervals about the object on a similar mounting apparatus M adapted for a different number of sources. If a suitably large number of such sources S are used, the rotating capability of the mounting apparatus A will accordingly become less desirable. An odd number of sources S, algebraicly defined as 2N+1 sources, where N is any integer, is preferred.

The support plate 70 has a opening formed therein having a circumference defined by the edge 70a which is slightly smaller than the aperture formed by the circular ring 66 so that the circular ring can be mounted with the plate 70 for support. The support plate 70, in turn, is attached by suitable means to a shaft 72. The shaft 72 is mounted for rotational movement relative to the support frame 74 by connecting the ends of the shaft 72 through suitable pins or ball-and-socket joints to horizontal members 76 of the platform 74. In this manner, the mounting apparatus M can be tilted relative to the platform 74 to obtain scans at different angular orientations relative to the plane in which the object O is passed through the circular ring.

V. PROCESSING

As previously described, the scaler 50 in each detector D in an array transmits a digital signal representative of the number of primary photons detected during an exposure to the memory buffer B where such signals are temporarily stored for later transmission to the computer C for processing. Preferably, such signals from the detectors D within an array are then transmitted in parallel along a CPU bus to the computer C to decrease transmission time.

Figure 6:
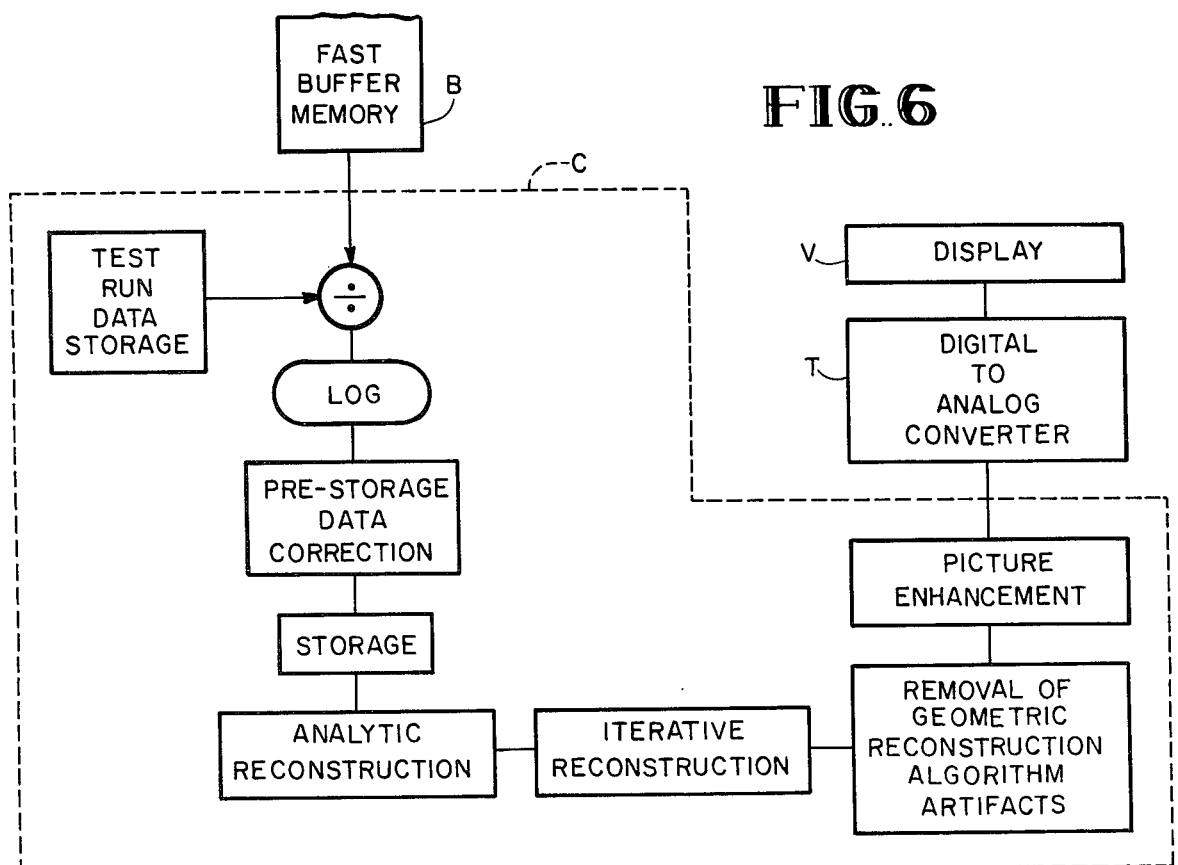
FIG. 6 is a schematic diagram of the process steps performed by the computer shown in FIG. 3.

The computer or microprocessor C (FIG. 6) divides the output signal from each detector D in the array with a test signal generated by the same detector D during a test run to obtain a signal representative of the fractional portion of the original radiation intensity which was transmitted from the source S along one of the paths P to the detector D. The natural logarithm of the fraction is then computed to determine a signal which represents the linear attenuation coefficient along the path.

Pre-storage correction of the signal is then accomplished using correction factors experimentally developed for the particular apparatus during test runs without an object O in place. These corrections eliminate non-linearities in the signals. Such correction factors also eliminate errors resulting from the "beam hardening" which occurs when X-ray radiation from X-ray tubes is used and from minor misalignments of the sources S and detectors arrays R. Errors caused by the response function of the detectors D can also be eliminated at this stage. The corrected signals are then placed into computer storage until the computer receives digital signals from each of the arrays R for the scan. If multiple scans are taken, the digital signals for each scan are stored until the end of the examination. For some reconstruction tomographic techniques, each of the corrected signals in storage is then divided by the number of representative elements along the path associated with such signals to determine a first estimate of the coefficient of absorption of each of the elements. For example, the computer may be programmed according to the reconstructive tomographic method described in U.S. Pat. No. 3,778,614. Alternately, analytic reconstruction techniques such as those described in the article "Principles of Computer Assisted Tomography (CAT) in Radiographic and Radioisotopic Imaging" by Rodney A. Brooks and Giovani Di Chiro published in Vol. 21, No. 5, of PHYSICAL MEDICAL BIOLOGY at pages 689–732 (1976) may be used by programming the computer in accordance with such principles.

Preferably, the computer is programmed to employ a RADON-based analytic reconstruction technique, such as those based on the Fourier or Convolution reconstruction theorems, to form a first estimate of the linear attenuation coefficient of each pixel or element of the object, as described in the article mentioned above.

Then iterative reconstruction techniques can be employed to refine the estimate to obtain a final estimate of the attenuation coefficient. Such a combination of techniques uses the advantages of analytic reconstruction methods to reduce the computer time necessary to obtain a final coefficient of absorption for each element yet has the advantages of the accuracy found in iterative techniques without the corresponding disadvantage of enormous memory storage or slower computing time.

The matrix of coefficients corresponding to the matrix of elements defining the object is then processed by the computer to remove those portions of the coefficient estimates which are a result of the reconstruction algorithm artifacts, which are superimposed on the data. These artifacts are essentially due to the geometry of the scanning apparatus.

Preferably, conventional digital smoothing techniques may then be applied to the data in order to make the resulting data more suitable for visual display. It should be noted, however, that the accuracy of the visual representation of such digital techniques is better than the application of such digital smoothing techniques to data obtain from output signals generated by current integration methods for the same dosage level. This is due to the superior statistical accuracy of the output signals obtained by using photon counting. The resulting modified matrix of data may then be fed to a digital-to-analog converter T for converting the data to analog signals for the purpose of visually displaying the data on a cathode ray tube or other display apparatus. Alternately, the corrected data may be stored on tape for later use.

VI. OPERATION

In the operation of the examining apparatus of the present invention, the apparatus is initially calibrated by operating the apparatus during test runs without inserting an object into the object aperture. Next, an object, such as a human body, is inserted horizontally into the object aperture. Each of the sources S are then sequentially pulsed on by the control circuit 2 for a predetermined time, 100 milliseconds for example, so that a planar section of the object is erradicated by sets of rays disposed at different mean angular positions. The time between pulses may be less than 1 millisecond so that a scan at the particular angular orientation of the sources can be accomplished more quickly than moving a source around the object.

The scalers 50 of the detector array R associated with a source is activated after a very short delay in order that the detector array counts only photons reaching the scintillators 10 from the activated source opposite it. The output signal from the scaler are then transmitted to the memory buffer B and subsequently to the computer C where the signals are corrected as hereinabove described and then stored.

After each of the sources S are pulsed to obtain a scan of the object, the mounting apparatus M may be rotated so that the sources S transmits at a different set of mean angular positions. The number of such scans of a given planar section, of course, will depend on the particular application in which the examining apparatus is employed. If desired, the mounting apparatus M may be tilted relative to the body to obtain scans of different planar sections which intersect.

The body may then be further inserted through the object aperture and multiple scans taken of a planar section adjacent to the first planar section scanned.

Again, the mounting apparatus A may be tilted to obtain scans of another set of planar sections which intersect.

After the desired number of scans is taken of the object, the corrected output signals stored in the computer C are processed using a suitable reconstruction technique to obtain the attenuation coefficient of each of the matrix elements into which the body is divided. Such computer attenuation coefficients is then used to reconstruct an image of the object which may be visually displayed or stored on magnetic tape for later use.

The foregoing disclosure and description of the invention are illustrative and explanatory thereof, and various changes in the size, shape, and materials as well as in the details of the illustrated construction may be made without departing from the spirit of the invention.

What is claimed is:

1. Radiographic apparatus for determining the intensity of penetrating radiation passing through an object as a plurality of penetrating ray photons along a plurality of respective paths from a radiation source; comprising:
   (a) high-speed scintillator means having a very fast decay time for detecting the plurality of penetrating ray photons passing through the object along one of the plurality of paths and converting the energy of the penetrating ray photons into a plurality of light photons within a sufficiently short time interval after detection such that substantially all light photons associated with each detected penetrating ray photon are generated within different time intervals;
   (b) photomultiplier means optically coupled to said scintillator means for detecting the light photons associated with each penetrating ray photon detected and generating a signal for each plurality of light photons associated with a penetrating ray photon detected; and
   (c) counting means for counting the signals generated by said photomultiplier means and generating output signals representative of the number of penetrating ray photons detected.

2. The apparatus of claim 1 wherein:
said scintillator means has a wall lining absorbent of penetrating ray photons so as to be self-collimating.

3. The apparatus of claim 2, wherein:
   (a) a portion of the penetrating ray photons transmitted from said radiation source is deflected by the object from its initial path to form secondary photons of penetrating radiation;
   (b) the photons transmitted through the object along the plurality of paths are primary photons; and
   (c) said scintillator means has a longitudinal axis and detects primary and secondary photons whose paths are within a small angular deviation from the longitudinal axis.

4. The apparatus of claim 3, wherein:
   (a) said photomultiplier means generates a primary signal for each primary photon detected and a secondary signal for each secondary photon detected; and
   (b) said counting means comprises:
      (1) discriminator means for discriminating between primary and secondary signals received from said photomultiplier means and generating event signals for each primary signal received; and
      (2) primary signal counter means for counting the number of event signals and generating output signals representative of the number of primary signals counted whereby the intensity of the penetrating radiation passing through the object along the path is determined.

5. A method of detecting the intensity of penetrating radiation passing through an object as a plurality of penetrating ray photons along a plurality of paths comprising the steps of:
   (a) detecting individual penetrating ray photons;
   (b) converting each individual penetrating ray photon detected into a plurality of light photons within a sufficiently short time interval after detection such that substantially all light photons associated with the penetrating ray photons detected are generated within different time intervals;
   (c) detecting the plurality of light photons generated by the conversion of each of said penetrating ray photons;
   (d) generating a primary signal of each plurality of light photons detected;
   (e) counting the number of primary signals generated; and
   (f) generating an output signal representative of the number of primary signals generated whereby the intensity of the penetrating radiation is determined by counting the number of penetrating ray photons detected.

6. Radiographic apparatus for determining the intensity of penetrating radiation passing through an object as a plurality of penetrating ray photons along a plurality of respective paths from a radiation source; comprising:
   scintillator means for detecting the plurality of penetrating ray photons passing through the object along one of the plurality of paths wherein said scintillator means has a wall lining absorbent of penetrating ray photons so as to be self-collimating.

7. The apparatus of claim 6, wherein said scintillator means comprises:
   (a) a scintillator of a suitable geometric configuration for collimating and detecting penetrating ray photons, said scintillator having an entry surface through which penetrating ray photons enter said scintillator, at least one lateral surface about said entry surface, and a longitudinal axis;
   (b) lining means disposed along said lateral surface for absorbing penetrating ray photons entering said scintillator whose paths are at a substantial angular deviation from a path parallel to said longitudinal axis and which are not detected prior to the time such photons reach said lateral surface.

8. The apparatus of claim 7, wherein:
   (a) said apparatus further comprises photomultiplier means optically coupled to said scintillator for detecting the light photons associated with each penetrating ray photon detected and generating a signal representative of the penetrating ray photons detected; and
   (b) said scintillator is configured to collimate and guide light photons.

9. The apparatus of claim 8, wherein said scintillator means further comprises:
   reflector means disposed between said lining means and said lateral surface of said scintillator for increasing the collimating efficiency of said scintillator means whereby the light photons generated by the detection of penetrating ray photons are collimated and efficiently guided a substantial distance to said photomultiplier means.

10. The apparatus of claim 7, further comprising:
a second scintillator disposed adjacent the lining means of said first scintillator such that said lining means prevents penetrating ray photons which enter said first scintillator from interacting with said second scintillator.

11. The apparatus of claim 10, further comprising:
(a) first photomultiplier means optically coupled to said first scintillator for detecting the light photons associated with each penetrating ray photon detected and generating a signal representative of the penetrating ray photons detected;
(b) second photomultiplier means optically coupled to said second scintillator for detecting the light photons associated with each penetrating ray photon detected and generating a signal representative of the penetrating ray photons detected; and
(c) wherein said adjacent first and second scintillators have different geometric configurations so that said photomultiplier means optically coupled to said scintillators are positioned in different planes, thereby allowing dense packing of said scintillator means regardless of the size of said photomultiplier means.

12. The apparatus of claim 7, wherein:
said scintillator is composed of material suitable for producing sufficient travel distance between entry of penetrating ray photons and detection of said penetrating ray photons so that the photons entering said scintillator whose paths are at a substantial angular deviation from a path parallel to said longitudinal axis are absorbed by said lining means before detection.

13. The apparatus of claim 12, wherein said scintillator comprises:
scintillating plastic.

14. The apparatus of claim 7, wherein:
the width of said entry surface is sized so that substantially all of the penetrating ray photons detected pass through said entry surface and have paths within a small angular deviation from a path parallel to said longitudinal axis.

15. The apparatus of claim 14 wherein:
the length of said scintillator is sufficiently long to allow photons which have paths within a smaller angular deviation from a path parallel to said longitudinal axis sufficient distance within said scintillator to be detected.

16. Apparatus for determining the intensity of penetrating ray photons passing through an object as a plurality of penetrating ray photons along a plurality of respective paths from a radiation source; comprising:
(a) scintillator means for detecting the penetrating ray photons and converting energy from penetrating ray photons into light photons, said scintillator means comprising:
(1) plastic scintillator of a suitable geometric configuration having an entry surface through which penetrating ray photons enter said scintillator, and at least one lateral surface about said entry surface which collimates both the penetrating ray photons and the light photons and which guide the light photons; wherein
(i) said scintillator having a longitudinal axis;
(ii) the width of said entry surface is sized so that substantially all of the penetrating ray photons detected pass through said entry surface and have paths within a small angular deviation from a path parallel to said longitudinal axis; and
(iii) the length of said scintillator is sufficiently long to allow photons which have paths within a small angular deviation from a path parallel to said longitudinal axis a sufficient travel distance within said scintillator to be detected;
(2) lining means disposed along said lateral surface for absorbing penetrating ray photons entering said scintillator whose paths are at a substantial angular deviation from a path parallel to said longitudinal axis and which are not detected prior to the time such photons reach said lateral surface;
(3) reflector means disposed between said lining means and said lateral surface for increasing the collimating efficiency and guiding efficiency of said scintillator means for light photons; and
(b) means optically coupled to said scintillator means for detecting the light photons and generating a signal representative of the penetrating ray detected.

* * * * *